US005768134A

United States Patent [19]
Swaelens et al.

[11] Patent Number: 5,768,134
[45] Date of Patent: Jun. 16, 1998

[54] METHOD FOR MAKING A PERFECTED MEDICAL MODEL ON THE BASIS OF DIGITAL IMAGE INFORMATION OF A PART OF THE BODY

[75] Inventors: Bart Swaelens, Putte; Wilfried Vancraen, Huldenberg, both of Belgium

[73] Assignee: Materialise, Naamloze Vennootschap, Huldenberg, Belgium

[21] Appl. No.: 722,155

[22] PCT Filed: Apr. 11, 1995

[86] PCT No.: PCT/BE95/00033

§ 371 Date: Oct. 18, 1996

§ 102(e) Date: Oct. 18, 1996

[87] PCT Pub. No.: WO95/28688

PCT Pub. Date: Oct. 26, 1995

[30] Foreign Application Priority Data

Apr. 19, 1994 [BE] Belgium .................... 9400399

[51] Int. Cl.$^6$ .................... G06F 19/00; G06T 15/00
[52] U.S. Cl. .................... 364/468.28; 623/16; 623/901; 433/201.1
[58] Field of Search .................... 364/468.03, 468.04, 364/468.25–468.27, 474.05, 474.24; 395/118–120, 124; 623/901, 11, 16; 128/653.1; 345/419, 420, 424; 433/201.1–204

[56] References Cited

U.S. PATENT DOCUMENTS

| | | | |
|---|---|---|---|
| 4,436,684 | 3/1984 | White | 364/474.05 |
| 4,704,686 | 11/1987 | Aldinger | 364/474.05 |
| 5,360,446 | 11/1994 | Kennedy | 623/16 |
| 5,448,489 | 9/1995 | Reuben | 364/474.05 |
| 5,503,149 | 4/1996 | Beaven | 128/653.1 |

FOREIGN PATENT DOCUMENTS 0 535 984 A1  7/1993  European Pat. Off. ......... G03C 9/08

OTHER PUBLICATIONS

*Australasian Physical & Engineering Sciences in Medicine Journal*, vol. 16, No. 2, Jun. 1993–pp. 79–85.

Primary Examiner—Reba I. Elmore
Assistant Examiner—Steven R. Garland
Attorney, Agent, or Firm—Bacon & Thomas

[57] ABSTRACT

A method is set fourth for making a perfected medical model on the basis of digital image information of a part of the body. According to which this image information of a part of the body is converted, by means of what is called the rapid prototyping technique and thus with a processing unit (4) and a rapid prototyping machine (5), into a basic model (9) of which at least a part perfectly shows the positive or negative form of at least a portion of the part of the body. At least an artificial functional element (10) with a useful function is added to the basic model (6) as a function of the digital information and possibly as a function of additional external information.

10 Claims, 3 Drawing Sheets

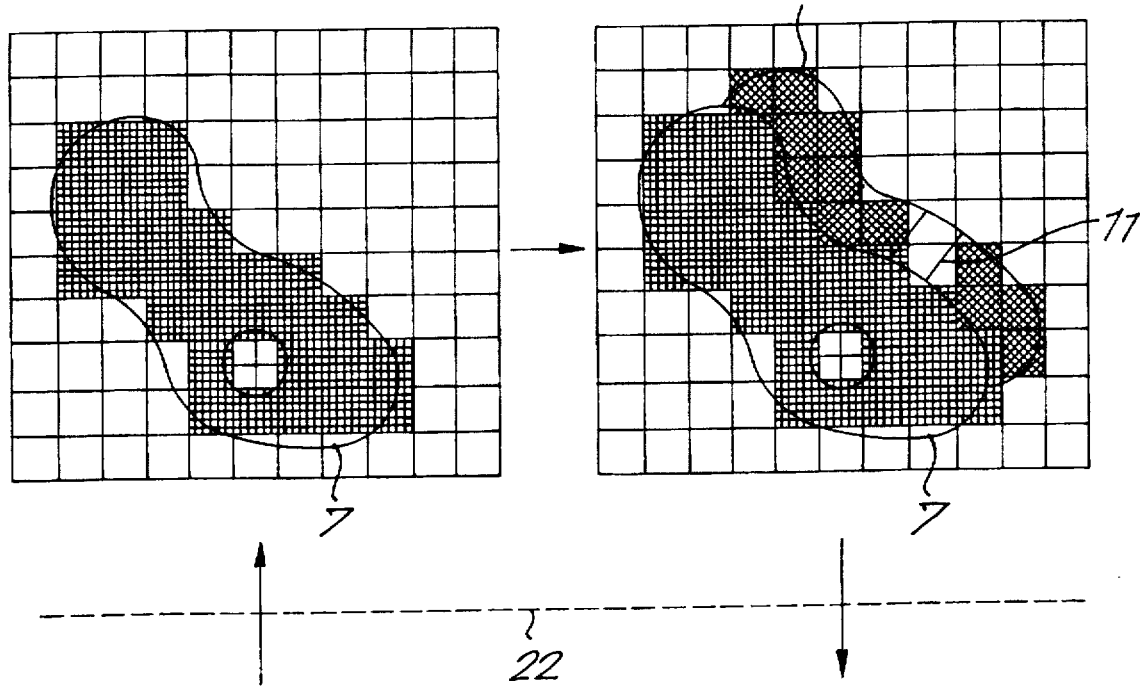
Fig. 2
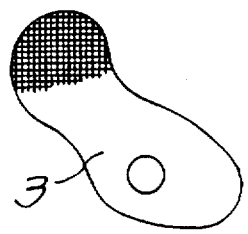 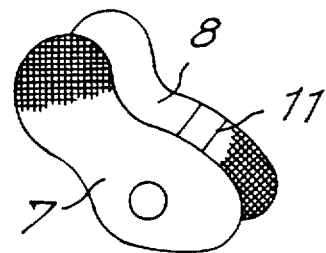
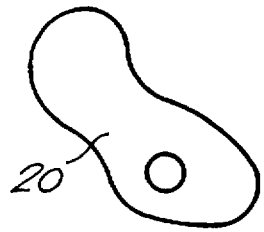 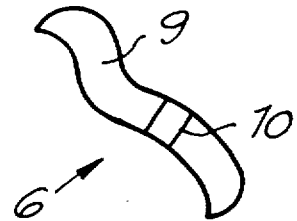

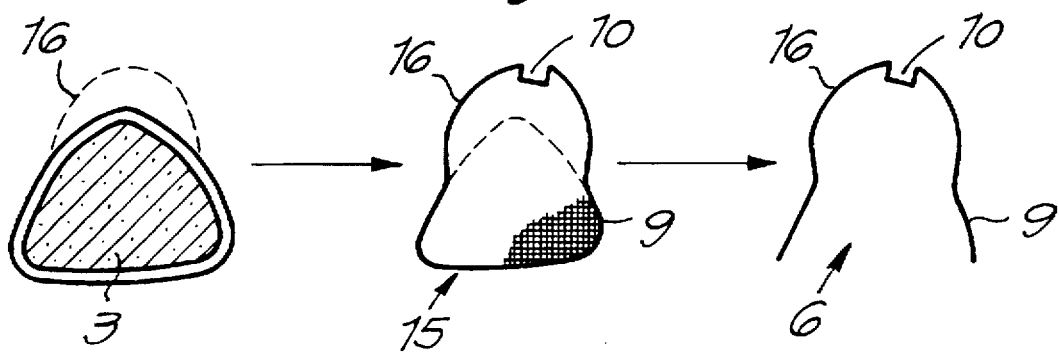
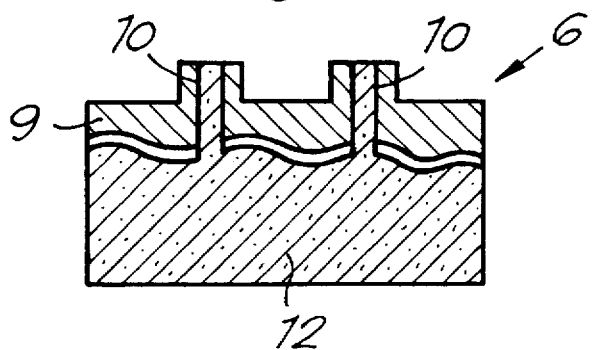
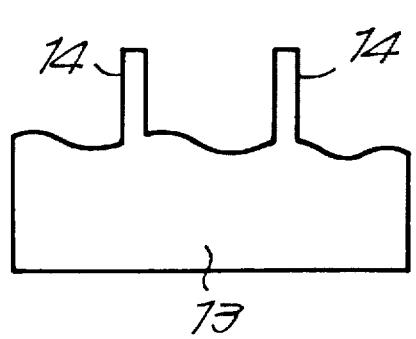
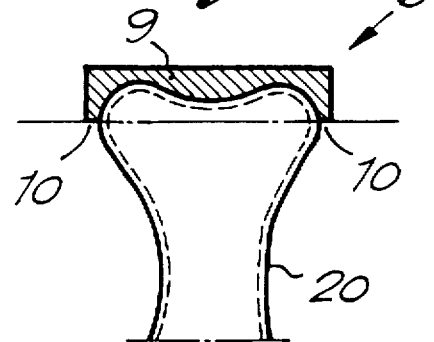
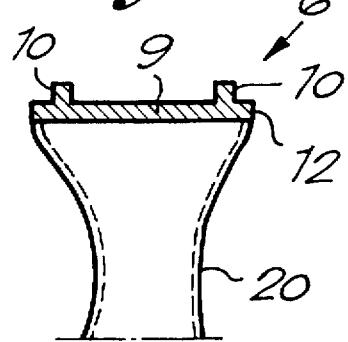

METHOD FOR MAKING A PERFECTED MEDICAL MODEL ON THE BASIS OF DIGITAL IMAGE INFORMATION OF A PART OF THE BODY

FIELD OF THE INVENTION

The invention concerns a method for making a medical model on the basis of digital image information of a part of the body, according to which this image information of a part of the body is converted, by means of what is called the rapid prototyping technique and thus with a processing unit and a rapid prototyping machine, into a basic model of which at least a part shows the positive or negative form of at least a portion of the part of the body.

BACKGROUND OF THE INVENTION

By rapid prototyping technique should be understood all techniques whereby an object is built layer by layer or point per point by adding or hardening material (also called free-form manufacturing). The best known techniques of this type are: stereo lithography and related techniques, whereby for example a basin with liquid synthetic material is selectively cured layer by layer by means of a computer-controlled electromagnetic beam; selective laser sintering, whereby powder particles are sintered by means of an electromagnetic beam or are welded together according to a specific pattern; or fused deposition modelling, whereby a synthetic material is fused and is stacked according to a line pattern.

The digital image information can be provided by a computer tomography scanner.

The model produced up to now according to the above-mentioned technique, can be a model which is an exact copy of the part of the body, for example a piece of bone, and upon which a surgery operation can be practiced, or it can be a prosthesis which fits perfectly to the part of the body.

However, the models produced up to now, including three-dimensional images, do not take advantage of all the information contained in the image information. They form a perfect copy of the part of the body, but they do not contain any additional functional elements.

Such models which are exact copies of real structures are for example produced from medical images with the technique disclosed in the article "Integration of 3-D medical imaging and rapid prototyping to create stereolithographic models" from T.M.BARKER et al., published in "Australasian Physical & Engineering Sciences in Medicine", vol. 16, no. 2, June 1993, pages 79–85.

Scanner data are transformed to a suitable format in a computer and the images are processed as a volume of voxels. The object is segmented prior to the meshing of the object surface and the creation of the stereolithographic model. The obtained model cannot be used for registration, this is finding back a position on the patient.

Functional elements, such as an opening indicating the place and direction for boring, can be added manually, but not as a function of the image information. At the time when these models are made, the grey value data of the image information are lost. However, these grey value data contain clinical data which are important for the use of the models. Such clinical data are for example the muscles and tendons which have to be taken into account when designing a prosthesis. These muscles and tendons are visible in the images, but not in the three-dimensional model, nor when working with segmented contours/surfaces in CAD-applications.

How to color selected elements of a three-dimensional object such as an anatomic model, prepared by irradiation techniques for example by stereolithography, is disclosed in EP-A-0 535 984, but this document does however neither disclose nor suggest to add artificial functional elements to the model for registration purposes, this is for transposing the pre-surgical planning or simulation to the surgery.

The manipulation of digital image data during the preparation of a surgical operation, for example, is known as such. It is possible, for example, to determine the position and direction of an implant on the images or to simulate surgeries. However, there is no connection with reality and, by lack of reference, these prepared image data cannot be used in practice. The image information is not used to the full extent.

As for the application of dental implants, attempts have already been made to use teeth of a provisional prosthesis as a reference. This provisional prosthesis is made on the basis of a mould. With a reconstruction by means of computer tomography scanner images on the basis of planes in which the bone is clearly visible, what is called a dental scan, one can see whether the position and the angle of the provisional teeth are correct in relation to the underlying bone, and one can make corrections. However, this is a time-consuming method.

Sometimes, a template is made on the basis of the mould and this template is used during the surgery. Only surface data are used hereby, so that part of the information of the dental scan remains unused.

Another method consists in making a model of the jaw by means of the rapid prototyping technique and to make a template on the basis of this model which is used during the surgery. The information of the digital image of the teeth (the dental scan) cannot be used either with this method.

SUMMARY OF THE INVENTION

The invention aims to remedy these disadvantages and to provide a method for making a perfected medical model on the basis of digital image information of a body part whereby the image information can be optimally used and can be put to use in practice.

This aim is reached according to the invention as at least one artificial functional element with a useful function is added to the basic model, as a function of the digital image information in the form in which all medical data are visible, this is in the grey value image information, before segmentation, the useful function of the functional element being an indication of a physical parameter, such as a position, a direction, a length or an angle which are important during surgery or the shape of a bone elevation.

External information coming from the medical user may be added to the image information, the artificial functional element being also as a function of this additional external information.

By subsequently converting the image with the additional information in information for the control of a rapid prototyping machine, there is a feedback of the medical data to reality and a perfected model is obtained which does not only have the shape of a certain part of the body, such as a ragged bone shape, and thus provides a perfect reference, but which also contains artificial elements which are added as a function of the image information and of possible new additional information, and which have a useful function.

The functional element is added as a function of the digital image information in the form in which all medical data are visible.

Such a form of the image information consists of the grey value information.

In a peculiar embodiment of the invention, the information on the basis of which the functional element is determined is processed factually in the perfected model by means of a voxel oriented computer system.

Via contour generation (segmentation/interpolation), one can switch from image processing to, for example, stereo lithography.

New information may be added from outside to determine the functional element, such information must then also be presented as voxels or contours.

The functional element with a useful function can be a shape, a color or a texture.

The method can be used in numerous applications.

Thus, it can be usefully applied in combination with the already applied computer aided surgery simulation, whereby bone segments are cut and moved at a certain angle and over a certain distance. With the help of the method, templates and jigs can be made which provide a perfect reference on the one hand and indicate angles and movements on the other hand.

The method can also be used for the preparation of tooth implants, whereby the perfected medical model is a template and the functional element is an opening or notch on the place where drilling is required, or for making a knee prosthesis, whereby the basic model is a metal base which can be joined to a sawn off tibia or femur and whereby the functional elements are orientation pins and/or fastening pins which stand on the base and which position and/or fix a prosthesis. Also an actual prosthesis can be made according to the method, part of which fits perfectly to existing bone and another part of which forms the functional element with a prosthetic function.

BRIEF DESCRIPTION OF THE DRAWINGS

In order to better explain the characteristics of the invention, the following preferred embodiments of a method for making a perfected medical model on the basis of digital image information of a part of the body are given as an example only without being limitative in any way, with reference to the accompanying drawings, in which:

FIG. 2 schematically shows how a perfected medical model is made on the basis of the image;

FIG. 3 schematically shows how another form of a perfected medical model is made according to the method of the invention;

FIGS. 4, 5, 6, 7 and 8 schematically show how yet other forms of perfected medical models for other applications can be made according to the invention.

DESCRIPTION OF THE INVENTION

Figure 1:
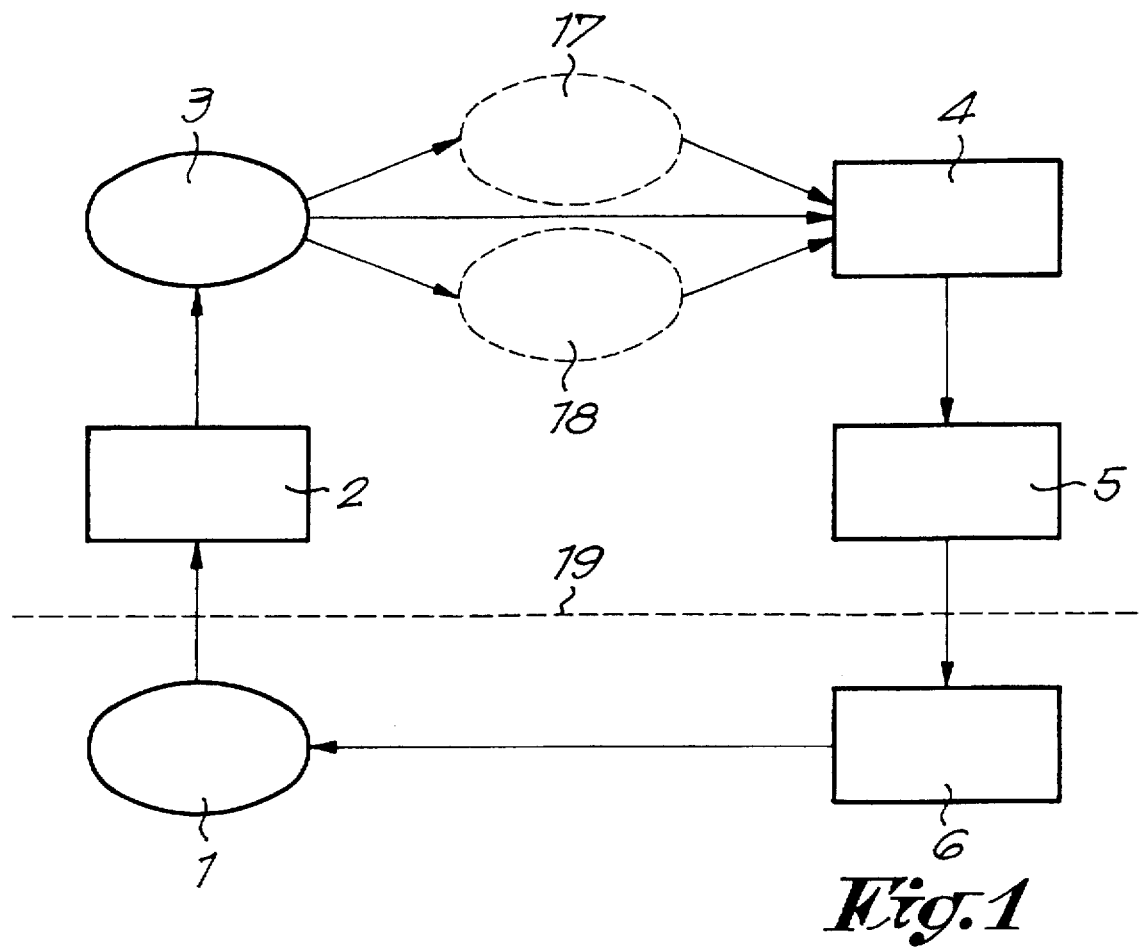
FIG. 1 shows a general block diagram of a method for making a perfected medical model according to the invention.

As is schematically represented in FIG. 1, images 3 are made of a part of the body of a patient 1 by means of a computer tomography scanner 2 or any other digital image processing unit such as a Magnetic Resonance Image machine, which thus contain digitized medical information.

Instead of converting these images in, for example, a three-dimensional image or a dental scan and subsequently either making a model by means of rapid prototyping or processing the images, the image data will be first processed in a processing unit 4, after which a perfected model 6 is made with these processed digitized image data by means of rapid prototyping with a rapid prototyping machine 5. Use can be made for this operation of a visual three-dimensional image 17 or a dental scan 18 which is derived in the usual manner from the images 3. This three-dimensional image 17 and this dental scan 18 are represented in FIG. 1 by means of a dashed line.

What is characteristic is that the model 6 can be used in reality on the patient 1 or in other words that the cycle represented in FIG. 1 is completed. In this figure, everything that is situated under the dashed line 19 represents reality, and everything that is situated above it is immaterial information.

The processing or preparation includes the manipulation of medical digital image data, possibly with additional digital information from outside, in such a way that an artificial, functional element 10 with a useful function is added to the produced basic model 9.

The processing of existing and possibly new information or the "design" is carried out with a voxel-oriented system in the processing unit 4, i.e., by means of voxels or contours, whereby voxels or groups of voxels are indicated in the images 3. A voxel is a three-dimensional pixel and thus represents a cube. The grey value data of the voxels can be used to obtain still higher resolutions and accuracies. The processing unit 4 which controls the rapid prototyping machine can help during the processing by carrying out operations on those voxels which are standard operations in three-dimensional image processing, such as thresholding (segmentation on the basis of grey values), three-dimensional reduction, expansion, region growing, boolean operations such as adding and subtracting, projections, etc.

If external technical elements are added, for example coming from a CAD system, these elements must be represented as voxels or contours as well. This can be easily done by means of cross section and shading algorithms.

After the interactive processing of the image information (for example rotations, translations, etc.), it is possible to go back to the original CAD data to obtain a higher resolution and accuracy of the functional element.

FIG. 2 shows an enlarged representation of one of the images 7 with grey values, derived in the processing unit 4 in the form of voxels from the images 3 of a bone 20 produced by the scanner 2. Through processing in the processing unit 4 are made negative images 8 in voxel form which fit perfectly to the images 7 and thus to the bone. Moreover, the image 11 of a functional element 10 is provided in voxel form in the images 8. The images 8 coincide with a reference part which forms a negative basic model 9 which fits perfectly to the bone, which basic model 9, together with the functional element 10, forms the perfected model 6.

In FIG. 2 is represented by means of a dashed line 21 the boundary between what is reality (underneath it) and what is image information (above it), whereas what is situated above the dashed line 22 is represented enlarged and in voxel form.

When providing the image 11 of the functional element 10 in voxel form, one can take into account all medical information contained in the images 7. Via stereo lithography, the images 8 having the images 1 1 of the artificial functional element 10 on top, are converted in the three-dimensional, factual, perfected model 6 which can be placed as a template on the bone of the patient 1 during a surgery and which fits perfectly to it. The useful function of the artificial functional element 10 can then be put to use. The information of the scanner 2 and the information of the position and direction of the artificial functional element 10 based upon it, are in this way used to the fullest extent and translated into reality.

In order to pass from the information of the processing unit 4 to the rapid processing technique, one can proceed as follows:

The information or data set, consisting of voxels and contours, of the processing unit 4 is converted into a set of contours per layer height. This is done by means of a screen which is finer than the screen of the original images 3, since the rapid prototyping techniques have a higher resolution than the scanner 2. In order to obtain this finer screen, use is made of the grey value information in the images 3. Thus, a pixel or voxel can partly belong to the perfected model 6 and partly not. This phenomenon is known as partial volume effect. When there are only two materials in one pixel or voxel, a contour line can be calculated in between the pixels by means of interpolation, as described by B. Swaelens and others in "Medical Applications of Rapid Prototyping Techniques", p. 107–120 of "Proceedings of the Fourth International Conference on Rapid Prototyping, Dayton, Ohio, Jun. 14–17, 1993". This higher resolution is important to make the designed model fit well onto the part of the body. Once the contours per layer are calculated, they are interpolated in the third dimension up to the layer height which is suitable for the rapid prototyping technique. This layer height is usually significantly lower than the scan distance.

Another method consists in converting the above-mentioned data set into a surface description with, for example, one of the usual formats such as triangle format. (STL). Such descriptions are used to calculate sections which are made by the rapid prototyping machine 5. Here also, it is possible to work with sub-voxel resolution.

According to a third method, the medical data or digital information is converted from the processing unit 4 to a CAD system. This is again approached by means of a surface description and by calculating the sections. It is possible to further add elements in the CAD system, but not as a function of the image information.

The artificial functional element 10 with a useful function can be a shape, a color, a texture or another characteristic element. The useful function of the element 10 can be the indication of a place where, a direction in which, a length over which, or an angle at which, one must cut, saw or drill; it can also be a point of attachment, the filing of an existing defect, a prosthetic function or an identification.

In the embodiment represented in FIG. 2, the perfected model 6 is a template and the artificial functional element 10 is an opening which indicates the position and direction for the boring bit of a boring machine. The basic model 9 forms a reference part. The thickness of the basic model 9 at the location of the opening determines the depth of hole.

The method can be used for the preparation of tooth implants. The position and the orientation of the implants, both in relation to the bone and in relation to the teeth, is very important. First, a dental scan is made. Thanks to computer-aided preparations, the thickness, position, direction and length of an implant can be well planned. By making a template according to the invention as represented in FIG. 2, it is not only possible to match the planned size and length of the implant in reality, but also directly the position and direction. A reference part is formed by the basic model 9 which fits perfectly to the bone and an element 10 which forms a guide for the boring bit with which the hole for the implant is drilled and which determines the position, direction and depth of the hole.

Instead of directly making a negative perfected model 6, a positive model 13–14 of the bone can be made in the above-described manner, but containing information regarding the position, direction and depth of the drill hole to be made in the form of protrusions 14 as represented in FIG. 3. A basic model 9 is made as a reference part only afterward, for example manually, with openings as functional elements 10, as a negative mould of the positive model 13–14 as is represented in FIG. 4.

Another application resides in the production of a membrane for bone generation, whereby this membrane can form the reference part or basic model 9 and the artificial functional element 10 is a notch or incision as represented in FIG. 5. First, a positive intermediate model 15 is made on the basis of the images 3 of the scanner 2, via stereo lithography, consisting of a basic model 9 and the required bone elevation 16 as a first artificial functional element 10. Whereas, according to known methods, the bone elevation is determined by realizing the elevation in reality in a radiographically visible material, prior to the scanning, the elevation is calculated according to the invention by the processing unit 4 and imported in the medical information derived from the grey value data, either departing from an ideal bone shape stored in a memory of the processing unit 4 or interactively.

A second artificial functional element 10 can be possibly provided, namely a place indication, for example in the shape of a notch, there where the implant should come. This can be either done through the agency of the user or automatically by means of a computer according to a stored program. In any case, it is preferably provided as a function of the grey value data in a dental scan.

From the intermediate model 15 is made a perfected model 6 in the shape of a membrane by making a mould on the basis of the intermediate model 15 and by shaping a foil in the mould into a membrane. Just like the intermediate model 15, the membrane is provided with a notch as an artificial functional element 10 which has as a function to indicate the place of the implant.

In the case where the implant is provided together with the membrane, reference marks or sutures can be provided as artificial functional elements 10 in the above-described manner to position the membrane in the space where the bone will grow later.

Another application of the method according to the invention consists in making prostheses.

With a knee prosthesis, the sliding surface of both the femur and the tibia must be replaced by sawing away a piece and by replacing this piece by a prosthesis. Hereby, it is important that the prosthesis fits correctly to the bone, especially on the side of the tibia, since there is only a thin wall of strong cortical bone there to support the prosthesis. When the prosthesis is too large, protruding edges form a problem.

In the first place, an incision is indicated in voxel form in the images 7, there where the tibia or femur should be sawn. A first negative model 6 is made in the above-described manner which fits perfectly to the bone 20, but which protrudes all round this bone 20 with an edge which is cut off by the incision. This edge then forms an artificial functional element 10 which serves as a guide for the saw with which the incision is sawn during the surgical operation.

The voxels above the incision are removed in the processing unit 4 and a base 12 is designed here as a reference part or basic model 9 upon which orientation pins are provided as artificial functional elements 10 by the processing unit 4. On the basis of this design is made, for example by means of stereo lithography and casting, a real model 6 which fits correctly to the remaining part of the bone 20 and which is provided with artificial functional elements 10 which are oriented in the right manner.

Figure 8:
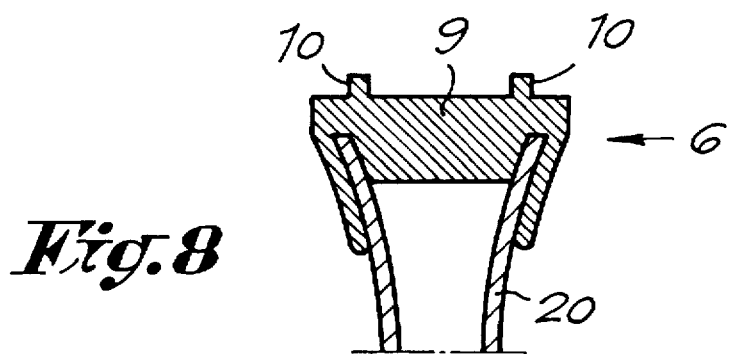

The base 12 can be designed such that it penetrates partly into the bone 20, and especially also partly surrounds the bone on the outside, as represented in FIG. 8. This largely increases the strength.

On the basis of the negative model 6 which forms the sawing template, and taking into account the thickness of the base and the position of the artificial functional elements 10, a positive model can be made of the prosthesis itself. One can hereby depart from the real model 6 of the sawing template or preferably from the digital information thereof in the processing unit 4 and calculate the prosthesis with the latter to finally transform it via rapid prototyping in a real prosthesis. This prosthesis will also be provided with artificial functional elements 10 which are complementary to those provided on the base 12.

Instead, a standard prosthesis can be provided on the base 12, whereby the artificial functional elements 10 on the basic model 9 formed by the base 12 need to be provided in this case as a function of complementary elements of the standard prosthesis.

A hip prosthesis can be made in an analogous manner which fits perfectly to the femur shaft on one side and which contains a technical part with functional elements on the other side upon which the artificial femur head can be placed. In the images 7 can be indicated the ideal length and the direction.

A prosthesis fitting perfectly to an existing structure on one side and bearing a technical part on the other side which has a prosthetic function can also be used for dorsal vertebra. Grey value data, for example regarding the position of the nerves, can be used in the processing unit 4 for the design of the prosthesis.

We claim:

1. In a method of making a medical model from digital information corresponding to a part of a human body wherein the digital information is used to generate information for rapid prototyping of the model, the improvement comprising:

adding to the digital information data related to at least one artificial functional element having a useful function related to a physical parameter and based on image information in the form in which all medical data are visible and including grey value image information, before segmentation;

carrying out the rapid prototyping of the model using the digital information with the added data whereby the medical model includes said artificial functional element.

2. The method according to claim 1, including, as part of said adding to the digital information step, adding external information from a source separate from the digital information.

3. The method according to claim 2, wherein said external information is used in the form of voxel or contour information.

4. The method according to claim 1, including processing at least said artificial image data used in producing said model using a voxel oriented computer system.

5. The method according to claim 1, wherein said functional element is selected from the group consisting of shape, color and texture.

6. The method according to claim 1, including rapid prototyping the model in the form of a reference part contoured to match a part of the body; and in said step of adding data related to at least one artificial functional element, adding data related to a guide for an instrument to be used on the body part, whereby the reference part will contain such guide.

7. The method according to claim 1, wherein said medical model comprises a reference part for use in a dental implant preparation procedure, and said image data is derived at least in part from a dental scan.

8. The method according to claim 1, wherein said model corresponds to a portion of bone on which additional bone is to be generated to a preselected height and includes as the artificial functional element the additional height corresponding to the additional bone to be generated; and using the model to form a metal foil and membrane including said additional height.

9. The method according to claim 8, including using the image data to form an added functional element of a notch in the model corresponding to the location of an implant to be placed in the bone before using the model to form said metal foil and membrane.

10. The method according to claim 1, wherein the medical model is a positive model made by rapid prototyping using the digital information and the image data to make a positive mold containing the functional element; and then making a negative mold of the part of the human body with the functional element by using the positive mold.

* * * * *